(12) United States Patent
Li et al.

(10) Patent No.: US 11,124,807 B2
(45) Date of Patent: Sep. 21, 2021

(54) SESQUITERPENE SYNTHASES FOR PRODUCTION OF DRIMENOL AND MIXTURES THEREOF

(71) Applicant: Firmenich SA, Satigny (CH)

(72) Inventors: Pan Li, Hangzhou (CN); Qi Wang, Shanghai (CN); Xiu-Feng He, Shanghai (CN); Olivier Haefliger, Geneva (CH)

(73) Assignee: Firmenich SA, Satigny (CH)

( * ) Notice: Subject to any disclaimer, the term of this patent is extended or adjusted under 35 U.S.C. 154(b) by 0 days.

(21) Appl. No.: 16/610,053

(22) PCT Filed: Apr. 27, 2018

(86) PCT No.: PCT/EP2018/060889
§ 371 (c)(1),
(2) Date: Oct. 31, 2019

(87) PCT Pub. No.: WO2018/202578
PCT Pub. Date: Nov. 8, 2018

(65) Prior Publication Data
US 2020/0056210 A1    Feb. 20, 2020

(30) Foreign Application Priority Data

May 3, 2017   (WO) ............... PCT/CN2017/082803
Jun. 7, 2017   (EP) ..................... 17174791

(51) Int. Cl.
| C12P 7/02 | (2006.01) |
| C12N 9/88 | (2006.01) |
| C12N 9/16 | (2006.01) |
| C12P 5/00 | (2006.01) |

(52) U.S. Cl.
CPC .............. *C12P 7/02* (2013.01); *C12N 9/88* (2013.01); *C12P 5/007* (2013.01); *C12Y 402/03126* (2015.07)

(58) Field of Classification Search
None
See application file for complete search history.

(56) References Cited

U.S. PATENT DOCUMENTS

2010/0192985 A1*  8/2010  Aehle ............... C11D 3/38645
                                                        134/26

FOREIGN PATENT DOCUMENTS

| WO | 2013058655 A1 | 4/2013 |
| WO | 2014150599 A1 | 9/2014 |
| WO | 2015086885 A1 | 6/2015 |
| WO | 2015169871 A2 | 11/2015 |
| WO | 2015176959 A1 | 11/2015 |

OTHER PUBLICATIONS

GenBank Database Accession No. KF874661, Dec. 2016, 2 pages (Year: 2016).*
Zhang et al., Structure 26:1474-1485, 2018 (Year: 2018).*
Kwon et al., FEBS Lett. 588:4597-4603, 2014 (Year: 2014).*
Goswami et al., Front. Onc. 9:297, 2019, 25 pages (Year: 2019).*
International Search Report and Written Opinion for International Application No. PCT/EP2018/060889, dated Apr. 27, 2018, 12 pages.
Tatiana et al., "Blast 2 Sequences, a new tool for comparing protein and nucleotide sequences", FEMS Microbiology Letters, Published May 15, 1999, pp. 247-250, vol. 174.
Chu et al.,"Identification, Functional Characterization, and Seasonal Expression Patterns of Five Sesquiterpene Synthases from Liquidambar formosana", Journal of Natural Products, Published May 25, 2018, pp. 1162-1172, vol. 31, No. 5.

* cited by examiner

*Primary Examiner* — David Steadman
(74) *Attorney, Agent, or Firm* — Armstrong Teasdale LLP

(57) ABSTRACT

Described herein is a method of producing drimenol and/or drimenol derivatives, the method including contacting at least one polypeptide with farnesyl diphosphate (FPP). The method may be performed in vitro or in vivo. Also described herein are amino acid sequences of polypeptides useful in the methods and nucleic acids encoding the polypeptides described. Also described herein are host cells or organisms genetically modified to express the polypeptides and useful to produce drimenol and/or derivatives of drimenol.

10 Claims, 5 Drawing Sheets

Specification includes a Sequence Listing.

SEQUENCE LISTING

<160> NUMBER OF SEQ ID NOS: 5

<210> SEQ ID NO 1
<211> LENGTH: 1674
<212> TYPE: DNA
<213> ORGANISM: Paeonia anomala
<220> FEATURE:
<221> NAME/KEY: misc_feature
<223> OTHER INFORMATION: cDNA

<400> SEQUENCE: 1

```
atgtctgtca aagttcctca atctcagaat gctcctacag aggttggacg tcggtccgta      60
aattttcatc ctactgtttg gggagatcgg tttatcacat acaataacca gtcagttgat     120
gatgatgtgg aaaagagatt aacaaagaa ctaaaatccc aagtgaggag aaagttggtg      180
gatgctgctg aaaatacatg tcagaagctt aacacaatcg atgcaatcga gagattaggc     240
ttggcttatc atttcgaaac agagattgaa gaagcactgc aaaatattta taattcctct     300
caggttgttg gaataatgt ggaagaagat gacctctact ctgttgcctt acgctttagg      360
cttctcagac aacagggcta caatatttca tctgatgtgt ttaacaaatt caagagatgat    420 aaagataact tcaaggtatc tttaattggt gatgcatcaa gcttgctaag cctatatgaa     480
```

-continued

```
gctgcacacc ttcgagtaca cggagaacac atactggatg aagctctaac tttctcagtt     540
aataatctgg aatcaatggc aacccaatta agtccacccc ttgcaacaca tgtaacccat     600
gcactaaaca gaccacttcg aaagggcatt ccaaggctag aagcaaggca ctacatttct     660
gtctacgaac aagatccttt acacgatgaa gatctattga agctcgcaaa gttagatttc     720
aaccaattac agaaaattca ccagaaggag ctaagcgaga tctcaaagtg gtggaaagat     780
ataaactttg tatcaaagct acctttgca agggacagag tggtggagtg ctacttttgg     840
ataatgtcag tgcatagcga gcccgagaac tggcttgcac gaaggacagc tgcaaaaata     900
gctgcggtaa cctccattat agatgatatc tatgatgtgc atggtacaat tgacgaactg     960
acgctattta cagaagccgt caacaggtgg gatataaaca acattgatca actcccggag    1020
tacatgaaaa tatgttataa ggcgctcttg ggcgttttta gtgaattagg ggaagagttg    1080
gaaaaacaag gaagatctta ccgcctcgat catacaattg aacttatgaa agatctagtt    1140
gggaactatt ttactgaatc gaatggttta agcgaaaaat atgtgcccac aatagaggag    1200
tatatgcgtg ctgcagaagt caccataggt tacaacaatg ctataactgc atcttttgcc    1260
acagccaaag ccggagatat tgcaaccaag gagacctttg aatgggtgtt gagtgaacct    1320
aaaattgtta aggcttcctc agtaatttgc aggttgatgg atgacttatc atcccacaag    1380
tttgagcaaa agagaggaca tgttgcatct gctattgaat gctacatgaa gcaacatgat    1440
gctacagagg aaaaggtgcg tgcggagttt aataaacaag tcaccgacgc ctggaaggtg    1500
ataaatcaag aatgtctcca cccaacagcc attccaatgc ctcttcttac atgtgttctc    1560
aactatgcac gtgtggctga tgtcatgtac aaggatggag atgcttatac atttgcccag    1620
atcttactga agatcatttt atcggcattg ttcaccgatc ctattgcaat gtga          1674
```

<210> SEQ ID NO 2
<211> LENGTH: 557
<212> TYPE: PRT
<213> ORGANISM: Paeonia anomala

<400> SEQUENCE: 2

```
Met Ser Val Lys Val Pro Gln Ser Gln Asn Ala Pro Thr Glu Val Gly
1               5                   10                  15

Arg Arg Ser Val Asn Phe His Pro Thr Val Trp Gly Asp Arg Phe Ile
                20                  25                  30

Thr Tyr Asn Asn Gln Ser Val Asp Asp Val Glu Lys Arg Leu Thr
            35                  40                  45

Lys Glu Leu Lys Ser Gln Val Arg Arg Lys Leu Val Asp Ala Ala Glu
        50                  55                  60

Asn Thr Cys Gln Lys Leu Asn Thr Ile Asp Ala Ile Glu Arg Leu Gly
65                  70                  75                  80

Leu Ala Tyr His Phe Glu Thr Glu Ile Glu Glu Ala Leu Gln Asn Ile
                85                  90                  95

Tyr Asn Ser Ser Gln Val Val Gly Asn Val Glu Glu Asp Asp Leu
                100                 105                 110

Tyr Ser Val Ala Leu Arg Phe Arg Leu Leu Arg Gln Gln Gly Tyr Asn
            115                 120                 125

Ile Ser Ser Asp Val Phe Asn Lys Phe Lys Asp Lys Asp Asn Phe
        130                 135                 140

Lys Val Ser Leu Ile Gly Asp Ala Ser Ser Leu Leu Ser Leu Tyr Glu
145                 150                 155                 160
```

Ala Ala His Leu Arg Val His Gly Glu His Ile Leu Asp Glu Ala Leu
            165                 170                 175

Thr Phe Ser Val Asn Asn Leu Glu Ser Met Ala Thr Gln Leu Ser Pro
            180                 185                 190

Pro Leu Ala Thr His Val Thr His Ala Leu Asn Arg Pro Leu Arg Lys
            195                 200                 205

Gly Ile Pro Arg Leu Glu Ala Arg His Tyr Ile Ser Val Tyr Glu Gln
210                 215                 220

Asp Pro Leu His Asp Glu Asp Leu Leu Lys Leu Ala Lys Leu Asp Phe
225                 230                 235                 240

Asn Gln Leu Gln Lys Ile His Gln Lys Glu Leu Ser Glu Ile Ser Lys
            245                 250                 255

Trp Trp Lys Asp Ile Asn Phe Val Ser Lys Leu Pro Phe Ala Arg Asp
            260                 265                 270

Arg Val Val Glu Cys Tyr Phe Trp Ile Met Ser Val His Ser Glu Pro
            275                 280                 285

Glu Asn Trp Leu Ala Arg Arg Thr Ala Lys Ile Ala Ala Val Thr
290                 295                 300

Ser Ile Ile Asp Asp Ile Tyr Asp Val His Gly Thr Ile Asp Glu Leu
305                 310                 315                 320

Thr Leu Phe Thr Glu Ala Val Asn Arg Trp Asp Ile Asn Asn Ile Asp
            325                 330                 335

Gln Leu Pro Glu Tyr Met Lys Ile Cys Tyr Lys Ala Leu Leu Gly Val
            340                 345                 350

Phe Ser Glu Leu Gly Glu Glu Leu Glu Lys Gln Gly Arg Ser Tyr Arg
            355                 360                 365

Leu Asp His Thr Ile Glu Leu Met Lys Asp Leu Val Gly Asn Tyr Phe
370                 375                 380

Thr Glu Ser Lys Trp Leu Ser Glu Lys Tyr Val Pro Thr Ile Glu Glu
385                 390                 395                 400

Tyr Met Arg Ala Ala Glu Val Thr Ile Gly Tyr Asn Asn Ala Ile Thr
            405                 410                 415

Ala Ser Phe Ala Thr Ala Lys Ala Gly Asp Ile Ala Thr Lys Glu Thr
            420                 425                 430

Phe Glu Trp Val Leu Ser Glu Pro Lys Ile Val Lys Ala Ser Ser Val
            435                 440                 445

Ile Cys Arg Leu Met Asp Asp Leu Ser Ser His Lys Phe Glu Gln Lys
450                 455                 460

Arg Gly His Val Ala Ser Ala Ile Glu Cys Tyr Met Lys Gln His Asp
465                 470                 475                 480

Ala Thr Glu Glu Lys Val Arg Ala Glu Phe Asn Lys Gln Val Thr Asp
            485                 490                 495

Ala Trp Lys Val Ile Asn Gln Glu Cys Leu His Pro Thr Ala Ile Pro
            500                 505                 510

Met Pro Leu Leu Thr Cys Val Leu Asn Tyr Ala Arg Val Ala Asp Val
            515                 520                 525

Met Tyr Lys Asp Gly Asp Ala Tyr Thr Phe Ala Gln Ile Leu Leu Lys
530                 535                 540

Asp His Leu Ser Ala Leu Phe Thr Asp Pro Ile Ala Met
545                 550                 555

<210> SEQ ID NO 3
<211> LENGTH: 1674
<212> TYPE: DNA

<213> ORGANISM: Artificial Sequence
<220> FEATURE:
<223> OTHER INFORMATION: codon optimized sequence

<400> SEQUENCE: 3

```
atgtccgtta aagttccgca aagccaaaat gccc ctaccg aagttggccg tcgttccgtc      60
aacttccacc cgacggtctg gggtgatcgt ttcattacct acaataacca gagcgttgac     120
gacgatgtgg aaaagcgttt gaccaaagaa ttgaagtccc aggtccgtcg taaactggtt     180
gacgctgcag agaacacttg ccagaaactg aacaccatcg acgcgatcga gcgcctgggt     240
ctggcttacc atttcgagac tgagattgaa gaggcactgc agaacatcta caattccagc     300
caagtcgtgg gcaataatgt agaggaagat gatttatata gcgtggcgct gcgttttcgt     360
ctgctgcgtc aacagggtta taacatcagc tccgatgtct ttaacaagtt caaagatgat     420
aaagacaatt tcaaggttag cctgatcggt gacgcaagct ctttgttatc tctgtatgaa     480
gccgcgcatc tgcgcgtgca tggcgagcat atcttggatg aagcgctgac ctttagcgtt     540
aataatctgg aatcgatggc aacccagctg agcccgccgc tggcaacgca cgttacgcac     600
gcgttgaacc gcccgctgcg caagggtatc ccgcgtctgg aagcgcgtca ttacatttct     660
gtgtacgaac aagatccact gcacgacgaa gatttgctta actggcgaa actggatttt     720
aatcaactgc aaaagattca ccagaaagaa ctgagcgaga ttagcaaatg gtggaaagac     780
attaatttcg tcagcaagct gccgttcgcc cgcgaccgtg ttgtggagtg ctatttctgg     840
attatgagcg ttcacagcga gcctgagaac tggctggcgc cgcaccgc ggctaagatt      900
gcggcagtca cgtcgattat cgacgatatc tatgacgtcc acggcaccat cgatgaactg     960
acgctgttca ccgaagccgt taaccgctgg gacatcaaca acattgatca gctgccggaa    1020
tacatgaaga tctgctacaa agcgctgctg ggcgtgttca gcgagctggg tgaagaactg    1080
gagaaacagg gtcgtagcta tcgcttggat cataccattg agctgatgaa agatctggtc    1140
ggtaattact tcaccgagtc caagtggctg agcgagaaat acgttccgac gatcgaagag    1200
tacatgcgtg ctgccgaagt gaccatcggt tacaacaatg ccattacggc atcttttgcc    1260
acggcaaagg ccggtgatat cgctaccaaa gaaacctttg aatgggtgct gagcgaaccg    1320
aagattgtca agcctccag cgttatttgt cgtctgatgg acgatttgag cagccataag    1380
tttgagcaaa agcgtggcca cgtcgcgagc gcgatcgagt gctatatgaa acagcacgac    1440
gcgaccgagg aaaaagttcg tgcagagttc aataaacaag tcaccgatgc gtggaaagtc    1500
attaaccaag agtgcttgca cccgacggcg atcccgatgc cactgctgac ctgtgtgctc    1560
aattatgcac gtgttgcgga cgttatgtat aaggatggtg acgcgtatac ctttgcgcaa    1620
attctgctga agaccaccct gagcgcactg ttcacggacc cgatcgcgat gtaa          1674
```

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
atgtctgtca aagttcctca atc         23

<210> SEQ ID NO 5
<211> LENGTH: 22
<212> TYPE: DNA
<213> ORGANISM: Artificial Sequence

```
<220> FEATURE:
<223> OTHER INFORMATION: Primer

<400> SEQUENCE: 5
tcacattgca ataggatcgg tg                                              22
```

SESQUITERPENE SYNTHASES FOR PRODUCTION OF DRIMENOL AND MIXTURES THEREOF

REFERENCE TO AN ELECTRONIC SEQUENCE LISTING

The contents of the electronic sequence listing (Sequence Listing.txt; Size: 9940 bytes; and Date of Creation: Oct. 31, 2019) is herein incorporated by reference in its entirety.

CROSS-REFERENCE TO RELATED APPLICATIONS

This application is a U.S. National Phase Application of PCT/EP2018/060889, filed on Apr. 27, 2018, which claims the benefit of priority to PCT/CN2017/082803, filed May 3, 2017, and also claims the benefit of priority to European Patent Application Number 17174791.8, filed Jun. 7, 2017, the entire contents of which are hereby incorporated by reference herein.

TECHNICAL FIELD

Provided herein are biochemical methods of producing drimenol and related compounds and derivatives and mixtures comprising drimenol, which method comprises the use of novel polypeptides.

BACKGROUND

Terpenes are found in most organisms (microorganisms, animals and plants). These compounds are made up of five carbon units called isoprene units and are classified by the number of these units present in their structure. Thus monoterpenes, sesquiterpenes and diterpenes are terpenes containing 10, 15 and 20 carbon atoms, respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

Biosynthetic production of terpenes involves enzymes called terpene synthases. There are numerous sesquiterpene synthases present in the plant kingdom, all using the same substrate (farnesyl diphosphate, FPP), but having different product profiles. Genes and cDNAs encoding sesquiterpene synthases have been cloned and the corresponding recombinant enzymes characterized.

Currently the main sources for drimenol are plants naturally containing drimenol; however, the contents of drimenol in these natural sources are low. Chemical synthesis approaches have been developed but are still complex and not cost-effective. There still remains a need for the discovery of new terpenes, terpene synthases and more cost-effective methods of producing drimenol and derivatives therefrom and mixtures comprising drimenol.

SUMMARY

Provided herein is a method for producing drimenol or a mixture comprising drimenol comprising:
a. contacting an acyclic farnesyl diphosphate (FPP) precursor with a polypeptide having sesquiterpene synthase activity, wherein the polypeptide comprises an amino acid sequence having at least 50%, 55%, 60%, 65%, 70%, 75%, 80%, 85%, 90%, 95%, 96%, 97%, 98% or 99% sequence identity to SEQ ID NO: 2 or comprises the amino acid sequence of SEQ ID NO: 2, to produce drimenol or a mixture comprising drimenol and one or more terpenes; and
b. optionally isolating the drimenol.

Also provided is a method that comprises transforming a host cell or non-human host organism with a nucleic acid encoding a polypeptide having drimenol synthase activity, wherein the polypeptide comprises an amino acid sequence having at least 50%, 55%, 60%, 65%, 70%, 75%, 80%, 85%, 90%, 95%, 96%, 97%, 98%, or 99% sequence identity to SEQ ID NO: 2 or comprises SEQ ID NO: 2.

Also provided is a method that further comprises culturing a non-human host organism or a host cell capable of producing FPP and transformed to express a polypeptide, wherein the polypeptide comprises an amino acid sequence having at least 55%, 60%, 65%, 70%, 75%, 80%, 85%, 90%, 95%, 98%, 99%, or 100% sequence identity to SEQ ID NO: 2 under conditions that allow for the production of the polypeptide.

In one aspect, the drimenol produced from the above methods is isolated.

In another aspect, the method further comprises contacting the drimenol with at least one enzyme to produce a drimenol derivative.

In a further aspect, the method comprises converting the drimenol to a drimenol derivative using chemical synthesis or biochemical synthesis.

Also provided herein is an isolated polypeptide having drimenol synthase activity comprising an amino acid sequence having at least 50%, 55%, 60%, 65%, 70%, 75%, 80%, 85%, 90%, 95%, 96%, 97%, 98% or 99% sequence identity to SEQ ID NO: 2 or comprising the amino acid sequence of SEQ ID NO: 2.

Further provided herein is an isolated nucleic acid molecule comprising a nucleotide sequence encoding a polypeptide having drimenol synthase activity and comprising an amino acid sequence having at least 50%, 55%, 60%, 65%, 70%, 75%, 80%, 85%, 90%, 95%, 96%, 97%, 98%, or 99% sequence identity to SEQ ID NO: 2 or comprising the amino acid sequence of SEQ ID NO: 2.

Further provided is an isolated nucleic acid comprising a nucleotide sequence having at least 75%, 80%, 85%, 90%, 95%, 96%, 97%, 98% or 99% sequence identity to SEQ ID NO: 1 or SEQ ID NO: 3 or comprising the nucleotide sequence of SEQ ID NO: 1 and SEQ ID NO: 3.

Further provided is an isolated nucleic acid molecule encoding a polypeptide provided herein.

In one aspect provided herein is a vector comprising the nucleic acid molecules described herein. In another aspect, the vector is an expression vector. In a further aspect, the vector is a prokaryotic vector, viral vector or a eukaryotic vector.

Also provided is a non-human host organism or a host cell comprising (1) a nucleic acid molecule described above, or (2) an expression vector comprising said nucleic acid molecule. In one aspect the non-human organism or host cell is a prokaryotic or eukaryotic cell. In another aspect the host cell is a bacterial cell, a plant cell, a fungal cell or a yeast. In a further aspect, the bacterial cell is *E. coli* and the yeast cell is *Saccharomyces cerevisiae*

Further provided is the use of a polypeptide described herein for producing drimenol or a mixture comprising drimenol and one or more terpenes.

In one aspect, the mixture produced in the above methods or uses comprises drimenol and nerolidol.

In a further aspect, the drimenol and/or nerolidol is isolated.

Figure 1:
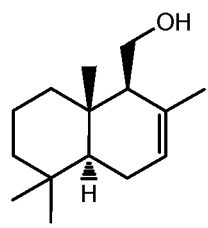
FIG. 1. Structure of (−)-drimenol.
Figure 2:
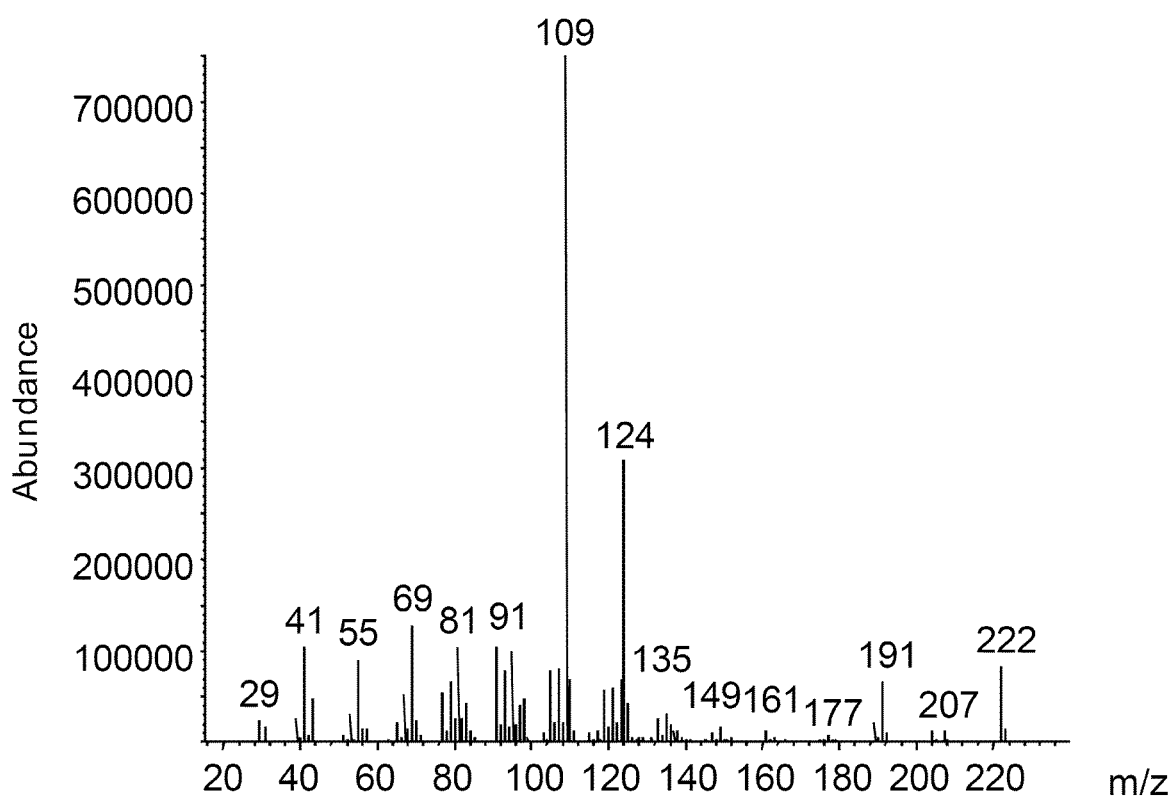
FIG. 2. Mass spectrum of authentic (−)-drimenol.
Figure 3:
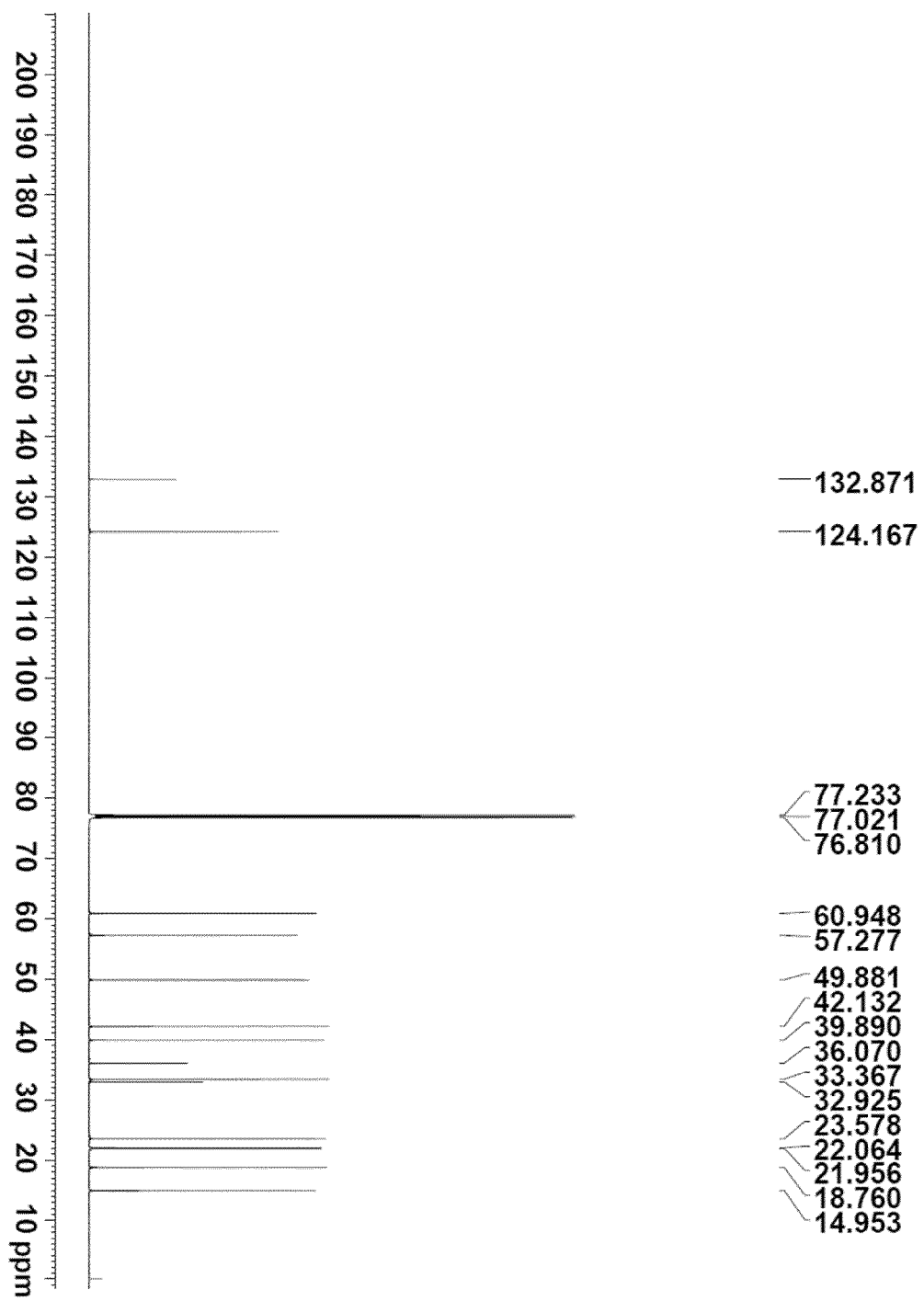
FIG. 3. $^{13}$C NMR spectrum of authentic (−)-drimenol.
Figure 4:
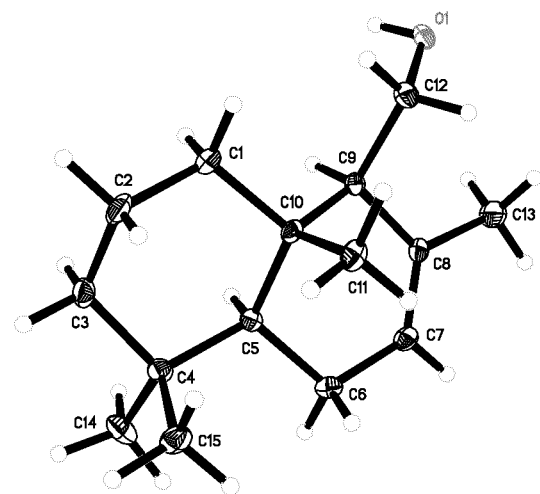
FIG. 4. X-Ray (Cu Kα radiation) structure of authentic (−)-drimenol.

ABBREVIATIONS USED bp base pair
kb kilo base
DNA deoxyribonucleic acid
cDNA complementary DNA
DTT dithiothreitol
FPP farnesyl diphosphate
GC gas chromatograph
IPTG isopropyl-D-thiogalacto-pyrano side
LB lysogeny broth
MS mass spectrometer/mass spectrometry
MVA mevalonic acid
PCR polymerase chain reaction
RNA ribonucleic acid
mRNA messenger ribonucleic acid
miRNA micro RNA
siRNA small interfering RNA
rRNA ribosomal RNA
tRNA transfer RNA Definitions The term "polypeptide" means an amino acid sequence of consecutively polymerized amino acid residues, for instance, at least 15 residues, at least 30 residues, at least 50 residues. In some embodiments herein, a polypeptide comprises an amino acid sequence that is an enzyme, or a fragment, or a variant thereof.

The term "protein" refers to an amino acid sequence of any length wherein amino acids are linked by covalent peptide bonds, and includes oligopeptide, peptide, polypeptide and full length protein whether naturally occurring or synthetic.

The term "isolated" polypeptide refers to an amino acid sequence that is removed from its natural environment by any method or combination of methods known in the art and includes recombinant, biochemical and synthetic methods.

The terms "sesquiterpene synthase" or "polypeptide having sesquiterpene synthase activity" relate to a polypeptide capable of catalyzing the synthesis of a sesquiterpene or a mixture comprising one or more sesquiterpenes, for example, drimenol and/or nerolidol, starting from an acyclic terpene pyrophosphate, particularly farnesyl diphosphate (FPP).

The terms "drimenol synthase" or "polypeptide having a drimenol synthase activity" or "drimenol synthase protein" relate to a polypeptide capable of catalyzing the synthesis of drimenol, in the form of any of its stereoisomers or a mixture thereof, starting from an acyclic terpene pyrophosphate, particularly farnesyl diphosphate (FPP). Drimenol may be the only product or may be part of a mixture of sesquiterpenes.

The terms "biological function," "function," "biological activity" or "activity" refer to the ability of the drimenol synthase to catalyze the formation of drimenol or a mixture of compounds comprising drimenol and one or more terpenes.

The terms "mixture of terpenes comprising drimenol" or "mixture of sesquiterpenes comprising drimenol" refer to a mixture of terpenes or sesquiterpenes that comprises drimenol and one or more additional terpenes or sesquiterpenes.

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material. The term "naturally-occurring" as used herein as applied to a nucleic acid refers to a nucleic acid that is found in a cell of an organism in nature and which has not been intentionally modified by a human in the laboratory.

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, N.Y., Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one regulatory sequence, which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

"Promoter" refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of drimenol or a mixture comprising drimenol and one or more terpenes in the cell or organism. Particularly, the nucleotide sequence encodes a polypeptide having drimenol synthase activity.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The term "primer" refers to a short nucleic acid sequence that is hybridized to a template nucleic acid sequence and is used for polymerization of a nucleic acid sequence complementary to the template.

As used herein, the term "host cell" or "transformed cell" refers to a cell (or organism) altered to harbor at least one nucleic acid molecule, for instance, a recombinant gene encoding a desired protein or nucleic acid sequence which upon transcription yields a drimenol synthase protein useful to produce drimenol or a mixture comprising drimenol and one or more terpenes. The host cell is particularly a bacterial cell, a fungal cell or a plant cell. The host cell may contain a recombinant gene which has been integrated into the nuclear or organelle genomes of the host cell. Alternatively, the host may contain the recombinant gene extra-chromosomally.

Homologous sequences include orthologous or paralogous sequences. Methods of identifying orthologs or paralogs including phylogenetic methods, sequence similarity and hybridization methods are known in the art and are described herein.

Paralogs result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

Orthologs, or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants producing drimenol synthase proteins.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

"Drimenol" for purposes of this application refers to (−)-drimenol (CAS: 468-68-8) (see also FIGS. 1-4).

The term "organism" refers to any non-human multicellular or unicellular organisms such as a plant, or a micro-organism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing FPP" when it produces FPP naturally or when it does not produce FPP naturally but is transformed to produce FPP, either prior to the transformation with a nucleic acid as described herein or together with said nucleic acid. Organisms or cells transformed to produce a higher amount of FPP than the naturally occurring organism or cell are also encompassed by the "organisms or cells capable of producing FPP".

For the descriptions herein and the appended claims, the use of "or" means "and/or" unless stated otherwise. Similarly, "comprise," "comprises," "comprising", "include," "includes," and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of."

DETAILED DESCRIPTION

The present invention particularly refers to the following embodiments:

1. A method for producing drimenol or a mixture comprising drimenol comprising:
    a. contacting an acyclic farnesyl diphosphate (FPP) precursor with a polypeptide having sesquiterpene synthase activity, wherein the polypeptide comprises an amino acid sequence having at least 50%, 55%, 60%, 65%, 70%, 75%, 80%, 85%, 90%, 95%, 96%, 97%, 98% or 99% sequence identity to SEQ ID NO: 2 or comprises the amino acid sequence of SEQ ID NO: 2, to produce drimenol or a mixture comprising drimenol and one or more terpenes; and
    b. optionally isolating the drimenol.
2. The method of embodiment 1, comprising transforming a host cell or non-human host organism with a nucleic acid encoding a polypeptide having drimenol synthase activity, wherein the polypeptide comprises an amino acid sequence having at least 50%, 55%, 60%, 65%, 70%, 75%, 80%, 85%, 90%, 95%, 96%, 97%, 98%, or 99% sequence identity to SEQ ID NO: 2 or comprises SEQ ID NO: 2.
3. The method of one of the preceding embodiments, further comprising culturing a non-human host organism or a host cell capable of producing FPP and transformed to express a polypeptide, wherein the polypeptide comprises an amino acid sequence having at least 55%, 60%, 65%, 70%, 75%, 80%, 85%, 90%, 95%, 98%, 99%, or 100% sequence identity to SEQ ID NO: 2 under conditions that allow for the production of the polypeptide.
4. The method of embodiment 1, wherein the drimenol is isolated.
5. The method of one of the preceding embodiments, comprising contacting the drimenol with at least one enzyme to produce a drimenol derivative.
6. The method of one of the preceding embodiments, comprising converting the drimenol to a drimenol derivative using chemical synthesis or biochemical synthesis.
7. An isolated polypeptide having sesquiterpene synthase activity comprising an amino acid sequence having at least 50%, 55%, 60%, 65%, 70%, 75%, 80%, 85%, 90%, 95%, 96%, 97%, 98% or 99% sequence identity to SEQ ID NO: 2 or comprising the amino acid sequence of SEQ ID NO: 2.
8. An isolated nucleic acid molecule
    a. comprising a nucleotide sequence encoding the polypeptide of embodiment 7;
    b. comprising a nucleotide sequence having at least 75%, 80%, 85%, 90%, 95%, 96%, 97%, 98% or 99% sequence identity to the nucleotide sequence of SEQ ID NO: 1 or SEQ ID NO: 3; or
    c. comprising the nucleotide sequence of SEQ ID NO: 1 or SEQ ID NO: 3.

9. A vector comprising
   a. the nucleic acid molecule of embodiment 8; or
   b. a nucleic acid encoding the polypeptide of embodiment 7.
10. The vector of embodiment 9, wherein the vector is a prokaryotic vector, viral vector or a eukaryotic vector.
11. The vector of one of the preceding embodiments, where the vector is an expression vector.
12. A host cell or a non-human host organism comprising
   a. the isolated nucleic acid of embodiment 8; or
   b. the vector of anyone of embodiments 9 to 11.
13. The method of anyone of embodiments 2 or 3, wherein the cell is a prokaryotic cell.
14. The method of embodiment 13, wherein the prokaryotic cell is a bacterial cell.
15. The method of embodiment 14, wherein the bacterial cell is *E. coli*.
16. The method of anyone of embodiments 2 or 3, wherein the cell is a eukaryotic cell.
17. The method of embodiment 16, wherein the eukaryotic cell is a yeast cell or a plant cell.
18. The method of embodiment 17, wherein the yeast cell is *Saccharomyces cerevisiae*.
19. Use of the polypeptide of embodiment 7 for producing drimenol or a mixture comprising drimenol and one or more terpenes.
20. The use of embodiment 19, wherein the mixture comprises drimenol and nerolidol.
21. The method of embodiment 1, wherein the mixture comprises drimenol and nerolidol.
22. The method of embodiment 21, wherein the drimenol and/or the nerolidol produced is isolated.

Additionally, provided herein is a nucleic acid molecule comprising a nucleotide sequence having at least 75%, 80%, 85%, 90%, 95%, 96%, 97%, 98% or 99% sequence identity to SEQ ID NO: 1 or SEQ ID NO: 3 or comprising the nucleotide sequence of SEQ ID NO: 1 or SEQ ID NO: 3 or the reverse complement thereof.

According to one embodiment, the nucleic acid molecule consists of a nucleotide sequence SEQ ID NO: 1 or SEQ ID NO: 3 or the reverse complement thereof.

In one embodiment, the nucleic acid of an embodiment herein can be either present naturally in *Paeonia* plants or in other plant species, or be obtained by modifying SEQ ID NO: 1 or SEQ ID NO: 3 or the reverse complement thereof.

In another embodiment, the nucleic acid is isolated or is derived from a plant of the Paeoniaceae family. In a further embodiment the nucleic acid is isolated or derived from *Paeonia anomala*.

Further provided is a nucleotide sequence obtained by modifying SEQ ID NO: 1 or SEQ ID NO: 3 or the reverse complement thereof which encompasses any sequence that has been obtained by modifying the sequence of SEQ ID NO: 1 or SEQ ID NO: 3, or of the reverse complement thereof using any method known in the art, for example, by introducing any type of mutations such as deletion, insertion and/or substitution mutations. The nucleic acids comprising a sequence obtained by mutation of SEQ ID NO: 1 or SEQ ID NO: 3 or the reverse complement thereof are encompassed by an embodiment herein, provided that the sequences they comprise share at least the defined sequence identity of SEQ ID NO: 1 or SEQ ID NO: 3 or the reverse complement thereof and provided that they encode a polypeptide having a drimenol synthase activity, as defined in any of the above embodiments. Mutations may be any kind of mutations of these nucleic acids, for example, point mutations, deletion mutations, insertion mutations and/or frame shift mutations of one or more nucleotides of the DNA sequence of SEQ ID NO: 1 or SEQ ID NO: 3. In one embodiment, the nucleic acid of an embodiment herein may be truncated provided that it encodes a polypeptide as described herein.

A variant nucleic acid may be prepared in order to adapt its nucleotide sequence to a specific expression system. For example, bacterial expression systems are known to more efficiently express polypeptides if amino acids are encoded by particular codons.

Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the drimenol synthase may be optimized for increased expression in the host cell. For example, nucleotides of an embodiment herein may be synthesized using codons particular to a host for improved expression.

In one embodiment provided herein is an isolated, recombinant or synthetic nucleic acid sequence of SEQ ID NO: 1 or SEQ ID NO: 3 encoding for a polypeptide having drimenol synthase activity comprising the amino acid sequence of SEQ ID NO: 2 or fragments thereof that catalyze production of drimenol or a mixture comprising drimenol and one or more terpenes in a cell from a FPP precursor.

Provided herein are also cDNA, genomic DNA and RNA sequences. Any nucleic acid sequence encoding the drimenol synthase or variants thereof is also referred herein as a drimenol synthase encoding sequence.

According to one embodiment, the nucleic acid of SEQ ID NO: 1 or SEQ ID NO: 3 is the coding sequence of a drimenol synthase gene encoding a drimenol synthase obtained as described in the Examples.

A fragment of a polynucleotide of SEQ ID NO: 1 or SEQ ID NO: 3 refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

It is clear to the person skilled in the art that genes, including the polynucleotides of an embodiment herein, can be cloned on basis of the available nucleotide sequence information, such as found in the attached sequence listing, by methods known in the art. These include e.g. the design of DNA primers representing the flanking sequences of such gene of which one is generated in sense orientations and which initiates synthesis of the sense strand and the other is created in reverse complementary fashion and generates the antisense strand. Thermo stable DNA polymerases such as those used in polymerase chain reaction are commonly used to carry out such experiments. Alternatively, DNA sequences representing genes can be chemically synthesized and subsequently introduced in DNA vector molecules that can be multiplied by e.g. compatible bacteria such as e.g. *E. coli.*

In a related embodiment provided herein, PCR primers and/or probes for detecting nucleic acid sequences encoding a drimenol synthase are provided. The skilled artisan will be aware of methods to synthesize degenerate or specific PCR primer pairs to amplify a nucleic acid sequence encoding the drimenol synthase or fragments thereof, based on SEQ ID NO: 1 or SEQ ID NO: 3. A detection kit for nucleic acid sequences encoding the drimenol synthase may include primers and/or probes specific for nucleic acid sequences encoding the drimenol synthase, and an associated protocol to use the primers and/or probes to detect nucleic acid sequences encoding the drimenol synthase in a sample. Such detection kits may be used to determine whether a plant, organism or cell has been modified, i.e., transformed with a sequence encoding the drimenol synthase.

To test a function of variant DNA sequences according to an embodiment herein, the sequence of interest is operably linked to a selectable or screenable marker gene and expression of the reporter gene is tested in transient expression assays with protoplasts or in stably transformed plants. The skilled artisan will recognize that DNA sequences capable of driving expression are built as modules. Accordingly, expression levels from shorter DNA fragments may be different than the one from the longest fragment and may be different from each other. Provided herein are also functional equivalents of the nucleic acid sequence coding the drimenol synthase proteins provided herein, i.e., nucleotide sequences that hybridize under stringent conditions to the nucleic acid sequence of SEQ ID NO: 1 or SEQ ID NO: 3.

The skilled artisan will be aware of methods to identify homologous sequences in other organisms and methods to determine the percentage of sequence identity between homologous sequences. Such newly identified DNA molecules then can be sequenced and the sequence can be compared with the nucleic acid sequence of SEQ ID NO: 1 or SEQ ID NO: 3.

The percentage of identity between two peptide or nucleotide sequences is a function of the number of amino acids or nucleotide residues that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web. Preferably, the BLAST program (Tatiana et al, *FEMS Microbiol Lett.,* 1999, 174:247-250, 1999) set to the default parameters, available from the National Center for Biotechnology Information (NCBI) website at ncbi.nlm.nih.gov/BLAST/b12seq/wblast2.cgi, can be used to obtain an optimal alignment of protein or nucleic acid sequences and to calculate the percentage of sequence identity.

A related embodiment provided herein provides a nucleic acid sequence which is complementary to the nucleic acid sequence according to SEQ ID NO: 1 or SEQ ID NO: 3 such as inhibitory RNAs, or nucleic acid sequence which hybridizes under stringent conditions to at least part of the nucleotide sequence according to SEQ ID NO: 1 or SEQ ID NO: 3. An alternative embodiment of an embodiment herein provides a method to alter gene expression in a host cell. For instance, the polynucleotide of an embodiment herein may be enhanced or overexpressed or induced in certain contexts (e.g. upon exposure to a certain temperature or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, provided herein is also an isolated, recombinant or synthetic polynucleotide encoding a polypeptide or variant polypeptide provided herein.

In one embodiment is provided an isolated nucleic acid molecule encoding a polypeptide having drimenol synthase activity and comprising an amino acid sequence having at least 50%, 55%, 60%, 65%, 70%, 75%, 80%, 85%, 90%, 95%, 96%, 97%, 98%, or 99% sequence identity to SEQ ID NO: 2 or comprising the amino acid sequence of SEQ ID NO: 2.

In one embodiment provided herein is an isolated polypeptide having sesquiterpene synthase activity and/or drimenol synthase activity and comprising an amino acid sequence having at least 50%, 55%, 60%, 65%, 70%, 75%, 80%, 85%, 90%, 95%, 96%, 97%, 98%, or 99% sequence identity to SEQ ID NO: 2 or comprising the amino acid sequence of SEQ ID NO: 2.

According to one embodiment, the polypeptide consists of the amino acid sequence of SEQ ID NO: 2.

In one embodiment, the polypeptide of an embodiment herein can be present naturally in *Paeonia* plants or in other plant species, or comprises an amino acid sequence that is a variant of SEQ ID NO: 2, either obtained by genetic engineering or found naturally in *Paeonia* plants or in other plant species.

According to another embodiment, the polypeptide is isolated or derived from a plant of the Paeoniaceae family. In a further embodiment, the polypeptide is isolated or derived from *Paeonia anomala.*

In one embodiment, the at least one polypeptide having sesquiterpene synthase activity and/or a drimenol synthase activity used in any of the herein-described embodiments or encoded by the nucleic acid used in any of the herein-described embodiments comprises an amino acid sequence that is a variant of SEQ ID NO: 2, obtained by genetic engineering. In one embodiment the polypeptide comprises an amino acid sequence encoded by a nucleotide sequence that has been obtained by modifying SEQ ID NO: 1 or SEQ ID NO: 3 or the reverse complement thereof.

Polypeptides are also meant to include variants and truncated polypeptides provided that they have sesquiterpene synthase activity and/or drimenol synthase activity.

According to another embodiment, the at least one polypeptide having a drimenol synthase activity used in any of the herein-described embodiments or encoded by the nucleic acid used in any of the herein-described embodiments comprises an amino acid sequence that is a variant of SEQ ID NO: 2, obtained by genetic engineering, provided that said variant has drimenol synthase activity and has the required percentage of identity to SEQ ID NO: 2 as described herein.

According to another embodiment, the at least one polypeptide having a drimenol synthase activity used in any of the herein-described embodiments or encoded by the nucleic acid used in any of the herein-described embodiments is a variant of SEQ ID NO: 2 that can be found naturally in other organisms, such as other plant species, provided that it has a drimenol synthase activity. As used herein, the polypeptide includes a polypeptide or peptide fragment that encompasses the amino acid sequences identified herein, as well as truncated or variant polypeptides provided that they have sesquiterpene synthase activity and/or a drimenol synthase activity and that they share at least the defined percentage of identity with the corresponding fragment of SEQ ID NO: 2.

Examples of variant polypeptides are naturally occurring proteins that result from alternate mRNA splicing events or from proteolytic cleavage of the polypeptides described herein. Variations attributable to proteolysis include, for example, differences in the N- or C-termini upon expression in different types of host cells, due to proteolytic removal of one or more terminal amino acids from the polypeptides of an embodiment herein. Polypeptides encoded by a nucleic acid obtained by natural or artificial mutation of a nucleic acid of an embodiment herein, as described thereafter, are also encompassed by an embodiment herein.

Polypeptide variants resulting from a fusion of additional peptide sequences at the amino and carboxyl terminal ends can also be used in the methods of an embodiment herein. In particular such a fusion can enhance expression of the polypeptides, be useful in the purification of the protein or improve the enzymatic activity of the polypeptide in a desired environment or expression system. Such additional peptide sequences may be signal peptides, for example. Another aspect encompasses methods using variant polypeptides, such as those obtained by fusion with other oligo- or polypeptides and/or those which are linked to signal peptides. Polypeptides resulting from a fusion with another functional protein, such as another protein from the terpene biosynthesis pathway, can also be advantageously used in the methods of an embodiment herein.

A variant may also differ from the polypeptide of an embodiment herein by attachment of modifying groups which are covalently or non-covalently linked to the polypeptide backbone. The variant also includes a polypeptide which differs from the polypeptide provided herein by introduced N-linked or O-linked glycosylation sites, and/or an addition of cysteine residues. The skilled artisan will recognize how to modify an amino acid sequence and preserve biological activity.

In addition to the gene sequences shown in the sequences disclosed herein, it will be apparent for the person skilled in the art that DNA sequence polymorphisms may exist within a given population, which may lead to changes in the amino acid sequence of the polypeptides disclosed herein. Such genetic polymorphisms may exist in cells from different populations or within a population due to natural allelic variation. Allelic variants may also include functional equivalents.

Further embodiments also relate to the molecules derived by such sequence polymorphisms from the concretely disclosed nucleic acids. These natural variations usually bring about a variance of about 1 to 5% in the nucleotide sequence of a gene or in the amino acid sequence of the polypeptides disclosed herein. As mentioned above, the nucleic acid encoding the polypeptide or variants thereof of an embodiment herein is a useful tool to modify non-human host organisms or cells and to modify non-human host organisms or cells intended to be used in the methods described herein.

An embodiment provided herein provides amino acid sequences of drimenol synthase proteins including orthologs and paralogs as well as methods for identifying and isolating orthologs and paralogs of the drimenol synthases in other organisms. Particularly, so identified orthologs and paralogs of the drimenol synthase retain drimenol synthase activity and are capable of producing drimenol or a mixture comprising drimenol and one or more terpenes starting from an acyclic terpene pyrophosphate precursor, e.g. FPP.

The polypeptide to be contacted with an acyclic terpene pyrophosphate, e.g. FPP, in vitro can be obtained by extraction from any organism expressing it, using standard protein or enzyme extraction technologies. If the host organism is an unicellular organism or cell releasing the polypeptide of an embodiment herein into the culture medium, the polypeptide may simply be collected from the culture medium, for example by centrifugation, optionally followed by washing steps and re-suspension in suitable buffer solutions. If the organism or cell accumulates the polypeptide within its cells, the polypeptide may be obtained by disruption or lysis of the cells and optionally further extraction of the polypeptide from the cell lysate. Intact cells, the cell lysate or the extracted polypeptide can be used to contact the acyclic terpene pyrophosphate for production of a terpene or a mixture of terpenes.

The polypeptide having a drimenol synthase activity, either in an isolated form or together with other proteins, for example in a crude protein extract obtained from cultured cells or microorganisms, may then be suspended in a buffer solution at optimal pH. If adequate, salts, DTT, inorganic cations and other kinds of enzymatic co-factors, may be added in order to optimize enzyme activity. The precursor FPP is added to the polypeptide suspension, which is then incubated at optimal temperature, for example between 15 and 40° C., particularly between 25 and 35° C., more particularly at 30° C. After incubation, the drimenol produced may be isolated from the incubated solution by standard isolation procedures, such as solvent extraction and distillation, optionally after removal of polypeptides from the solution.

According to another embodiment, the at least one polypeptide having a drimenol synthase activity can be used for production of drimenol or mixtures of terpenes comprising drimenol. In another embodiment, the mixture comprising drimenol may also comprise nerolidol.

One particular tool to carry out the method of an embodiment herein is the polypeptide itself as described herein.

According to a particular embodiment, the polypeptide is capable of producing a mixture of sesquiterpenes comprising drimenol. In a further embodiment, the synthase is capable of producing a mixture of sesquiterpenes comprising drimenol, wherein drimenol represents at least 20%, particularly at least 30%, particularly at least 35%, particularly at least 90%, particularly at least 95%, more particularly at least 98% of the sesquiterpenes produced. In another aspect provided here, the drimenol is produced with greater than or equal to 95%, more particularly 98% selectivity.

According to another embodiment, the sesquiterpene synthase is capable of producing a mixture of sesquiterpenes comprising drimenol and nerolidol. In a further embodiment, the synthase is capable of producing a mixture of sesquiterpenes comprising drimenol and nerolidol, wherein nerolidol represents at least 5% to about 80%, particularly at least 10% to about 80%, particularly at least 15% to about 80%, particularly at least 16% to about 80%, particularly at least 50% to about 80%, particularly at least 60% to about 80%, particularly at least 70% to about 80%, particularly about 79% of the sesquiterpenes produced.

The functionality or activity of any sesquiterpene synthase or drimenol synthase protein, variant or fragment, may be determined using various methods. For example, transient or stable overexpression in plant, bacterial or yeast cells can be used to test whether the protein has activity, i.e., produces one or more sesquiterpenes such as drimenol or a mixture of sesquiterpenes comprising drimenol or comprising drimenol and nerolidol from produce an acyclic terpene pyrophosphate precursor, e.g. FPP precursor. Drimenol synthase activity may be assessed in a microbial expression system, such as the assay described in Example 2 herein on the production of drimenol, indicating functionality. A variant or derivative of a drimenol synthase polypeptide of an embodiment herein retains an ability to produce drimenol or a mixture comprising drimenol from FPP precursors. Amino acid sequence variants of the drimenol synthases provided herein may have additional desirable biological functions including, e.g., altered substrate utilization, reaction kinetics, product distribution or other alterations.

The ability of a polypeptide to catalyze the synthesis of a particular sesquiterpene (for example drimenol) can be simply confirmed, for example, by performing the enzyme assay as detailed in Examples 1 and 2.

Further provided is at least one vector comprising the nucleic acid molecules described herein.

Also provided herein is a vector selected from the group of a prokaryotic vector, viral vector and a eukaryotic vector.

Further provided here is a vector that is an expression vector.

In one embodiment, several drimenol synthases encoding nucleic acid sequences are co-expressed in a single host, particularly under control of different promoters. In another embodiment, several drimenol synthase proteins encoding nucleic acid sequences can be present on a single transformation vector or be co-transformed at the same time using separate vectors and selecting transformants comprising both chimeric genes. Similarly, one or more drimenol synthase encoding genes may be expressed in a single plant, cell, organism, or microorganism together with other chimeric genes.

The nucleic acid sequences of an embodiment herein encoding drimenol synthase proteins can be inserted in expression vectors and/or be contained in chimeric genes inserted in expression vectors, to produce drimenol synthase proteins in a host cell or non-human host organism. The vectors for inserting transgenes into the genome of host cells are well known in the art and include plasmids, viruses, cosmids and artificial chromosomes. Binary or co-integration vectors into which a chimeric gene is inserted can also be used for transforming host cells.

An embodiment provided herein provides recombinant expression vectors comprising a nucleic acid sequence of a drimenol synthase gene, or a chimeric gene comprising a nucleic acid sequence of a drimenol synthase gene, operably linked to associated nucleic acid sequences such as, for instance, promoter sequences. For example, a chimeric gene comprising a nucleic acid sequence of SEQ ID NO: 1 or SEQ ID NO: 3 or a variant thereof may be operably linked to a promoter sequence suitable for expression in plant cells, bacterial cells or fungal cells, optionally linked to a 3' non-translated nucleic acid sequence.

Alternatively, the promoter sequence may already be present in a vector so that the nucleic acid sequence which is to be transcribed is inserted into the vector downstream of the promoter sequence. Vectors can be engineered to have an origin of replication, a multiple cloning site, and a selectable marker.

In one embodiment, an expression vector comprising a nucleic acid as described herein can be used as a tool for transforming non-human host organisms or host cells suitable to carry out the method of an embodiment herein in vivo.

The expression vectors provided herein may be used in the methods for preparing a genetically transformed non-human host organism and/or host cell, in non-human host organisms and/or host cells harboring the nucleic acids of an embodiment herein and in the methods for making polypeptides having a drimenol synthase activity, as described herein.

Recombinant non-human host organisms and host cells transformed to harbor at least one nucleic acid of an embodiment herein so that it heterologously expresses or over-expresses at least one polypeptide of an embodiment herein are also very useful tools to carry out the method of an embodiment herein. Such non-human host organisms and host cells are therefore provided herein.

In one embodiment is provided a host cell or non-human host organism comprising at least one of the nucleic acid molecules described herein or comprising at least one vector comprising at least one of the nucleic acid molecules.

A nucleic acid according to any of the above-described embodiments can be used to transform the non-human host organisms and cells and the expressed polypeptide can be any of the above-described polypeptides.

In one embodiment, the non-human host organism or host cell is a prokaryotic cell. In another embodiment, the non-human host organism or host cell is a bacterial cell. In a further embodiment, the non-human host organism or host cell is *Escherichia coli*.

In one embodiment, the non-human host organism or host cell is a eukaryotic cell. In another embodiment, the non-human host organism or host cell is a yeast cell. In a further embodiment, the non-human host organism or cell is *Saccharomyces cerevisiae*.

In a further embodiment, the non-human organism or host cell is a plant cell.

In one embodiment the non-human host organism or host cell expresses a polypeptide, provided that the organism or cell is transformed to harbor a nucleic acid encoding said polypeptide, this nucleic acid is transcribed to mRNA and the polypeptide is found in the host organism or cell.

Suitable methods to transform a non-human host organism or a host cell have been previously described and are also provided herein.

To carry out an embodiment herein in vivo, the host organism or host cell is cultivated under conditions conducive to the production of sesquiterpenes such as drimenol or a mixture comprising drimenol. Accordingly, if the host is a transgenic plant, optimal growth conditions can be provided, such as optimal light, water and nutrient conditions, for example. If the host is a unicellular organism, conditions conducive to the production of drimenol or a mixture comprising drimenol may comprise addition of suitable cofactors to the culture medium of the host. In addition, a culture medium may be selected, so as to maximize drimenol synthesis. Examples of optimal culture conditions are described in a more detailed manner in the Examples.

Non-human host organisms suitable to carry out the method of an embodiment herein in vivo may be any non-human multicellular or unicellular organisms. In one embodiment, the non-human host organism used to carry out an embodiment herein in vivo is a plant, a prokaryote or a fungus. Any plant, prokaryote or fungus can be used. Particularly useful plants are those that naturally produce high amounts of terpenes. In another embodiment the non-human host organism used to carry out the method of an embodiment herein in vivo is a microorganism. Any microorganism can be used, for example, the microorganism can be a bacteria or yeast, such as *E. coli* or *Saccharomyces cerevisiae*.

Some of these organisms do not produce FPP naturally. To be suitable to carry out the method of an embodiment herein, organisms or cells that do not produce an acyclic terpene pyrophosphate precursor, e.g. FPP, naturally are transformed to produce said precursor. They can be so transformed either before the modification with the nucleic acid described according to any of the above embodiments or simultaneously, as explained above. Methods to transform organisms, for example microorganisms, so that they produce an acyclic terpene pyrophosphate precursor, e.g. FPP, are already known in the art.

Isolated higher eukaryotic cells can also be used, instead of complete organisms, as hosts to carry out the method of an embodiment herein in vivo. Suitable eukaryotic cells may be any non-human cell, such as plant or fungal cells.

Further provided herein is a method of producing drimenol or a mixture comprising drimenol comprising:
 i) contacting an acyclic terpene pyrophosphate, particularly farnesyl diphosphate (FPP) with a polypeptide having drimenol synthase activity and comprising an amino acid sequence having at least 50%, 55%, 60%, 65%, 70%, 75%, 80%, 85%, 90%, 95%, 96%, 97%, 98%, or 99% sequence identity to SEQ ID NO: 2 or comprising the amino acid sequence of SEQ ID NO: 2 to produce drimenol or a mixture comprising drimenol and one or more terpenes; and
 ii) optionally isolating the drimenol.
In one aspect, the drimenol is isolated.

In another aspect provided here, the drimenol is produced with greater than or equal to 20%, 30%, 35%, 40%, 50%, 60%, 80%, or 90% or even 95% selectivity of the sesquiterpenes produced.

Further provided here is a method comprising transforming a host cell or a non-human host organism with a nucleic acid encoding a polypeptide having drimenol synthase activity and comprising an amino acid sequence having at least 50%, 55%, 60%, 65%, 70%, 75%, 80%, 85%, 90%, 95%, 96%, 97%, 98%, or 99% sequence identity to SEQ ID NO: 2 or comprising the amino acid sequence of SEQ ID NO: 2.

In one embodiment, a method provided herein comprises cultivating a non-human host organism or a host cell capable of producing FPP and transformed to express a polypeptide wherein the polypeptide comprises a sequence of amino acids that has at least 75%, 80%, 85%, 90%, 95%, 98%, 99% or 100% sequence identity to SEQ ID NO: 1 or SEQ ID NO: 3 under conditions that allow for the production of the polypeptide.

In another embodiment, a method provided herein comprises contacting a sesquiterpene such as drimenol with at least one enzyme to produce a sesquiterpene derivative. Examples of such derivatives of drimenol include but not limited to drimenyl acetate (CAS 40266-93-1), drimenal (CAS 105426-71-9), drimenic acid (CAS 111319-84-7).

According to another particularly embodiment, the method of any of the above-described embodiments is carried out in vivo. In such a case, step a) comprises cultivating a non-human host organism or a host cell capable of producing FPP and transformed to express at least one polypeptide comprising an amino acid comprising SEQ ID NO: 2 or a functional variant thereof and having a drimenol synthase activity, under conditions conducive to the production of one or more sesquiterpenes such as drimenol or a mixture comprising drimenol. Drimenol may be the only product or may be part of a mixture of sesquiterpenes. In one embodiment, the mixture of sesquiterpenes comprises drimenol and nerolidol.

According to a further embodiment, the method further comprises, prior to step a), transforming a non-human organism or cell capable of producing FPP with at least one nucleic acid encoding a polypeptide comprising an amino acid comprising SEQ ID NO: 2 or encoding a polypeptide having drimenol synthase activity and comprising an amino acid sequence having at least 50%, 55%, 60%, 65%, 70%, 75%, 80%, 85%, 90%, 95%, 96%, 97%, 98% or 99% sequence identity to SEQ ID NO: 2, so that said organism expresses said polypeptide.

These embodiments of an embodiment herein are particularly advantageous since it is possible to carry out the method in vivo without previously isolating the polypeptide. The reaction occurs directly within the organism or cell transformed to express said polypeptide.

An embodiment herein provides polypeptides of an embodiment herein to be used in a method to produce drimenol or a mixture comprising drimenol by contacting an FPP precursor with the polypeptides of an embodiment herein either in vitro or in vivo.

Further provided is the use of a polypeptide as described herein for producing drimenol or a mixture comprising drimenol and one or more terpenes or a mixture comprising drimenol and nerolidol. In one embodiment, the drimenol and/or nerolidol produced is isolated.

The following examples are illustrative only and are not intended to limit the scope of the claims an embodiments described herein.

EXAMPLES

Example 1

*Paeonia anomala* Plant Material Sourcing and Root Transcriptome Sequencing.

Figure 5:
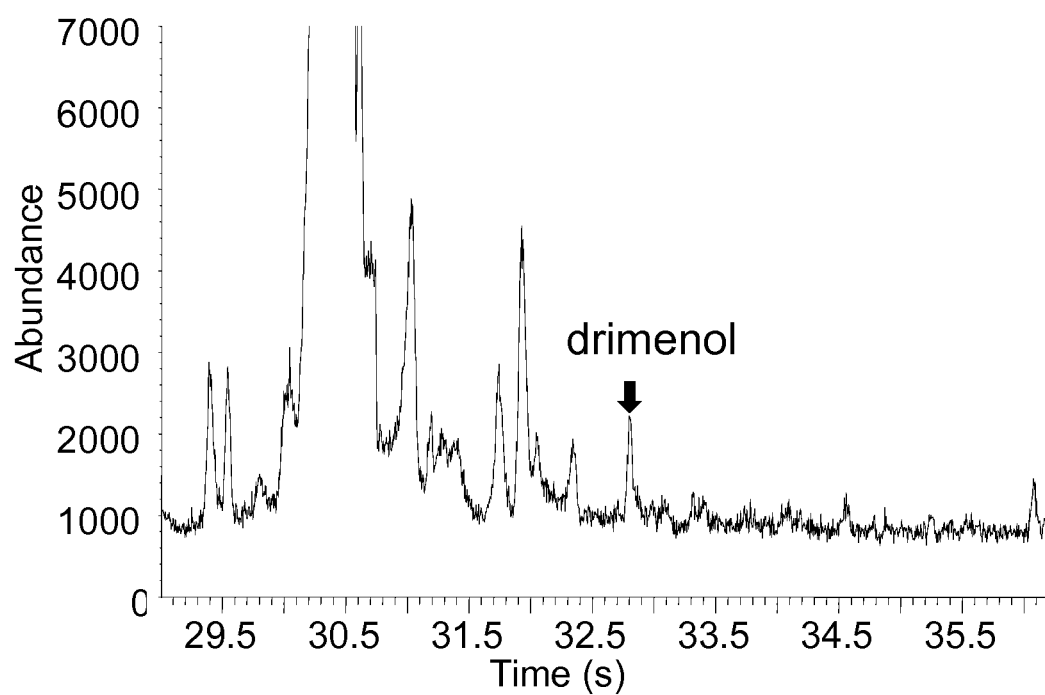
FIG. 5. Shows GC/MS chromatogram of *Paeonia anomala* root dichloromethane extract. Arrow denotes the peak of drimenol.

*Paeonia anomala* plant material was obtained from Datong in Qinghai, China. To establish if *Paeonia anomala* contained drimenol, its roots were collected and extracted fresh with dichloromethane for chemical analysis. The extract was analyzed by GC-MS, the parameters of GC-MS analysis were described as below: An Agilent 6890 series GC system equipped with a DB1-ms column 30 m×0.25 mm×0.25 μm film thickness, P/N 122-0132 (J&W scientific Inc., Folsom, Calif.) and coupled with a 5975 series mass spectrometer was used. The carrier gas was helium at a constant flow of 0.7 mL/min. Injection was in split (1:5) mode with the injector temperature set at 250° C. The oven temperature was programmed from 50° C. (5 min hold) to 300° C. at 5° C./min, then to 340° C. at 50° C./min and held for 3 min. Identification of products was based on mass spectra and retention index. The roots of *Paeonia anomala* contained a small amount of drimenol (FIG. 5).

Fresh roots of *Paeonia anomala* were used for transcriptome analysis. Total RNA was extracted using the Column Plant RNAout (TIANDZ, China). This total RNA was processed using the Illumina Total RNA-Seq technique and sequenced on Illumina MiSeq sequencer. A total of 9 million of paired-end reads of 2×251 bp were generated. The reads were assembled using the Trinity software. 26457 unigenes with an average size of 1109 bp were obtained. The unigenes were annotated by NCBI Blast as well as InterProScan software. This approach provided the sequences for 7 new putative sesquiterpene synthases including PaTPS3. The enzymatic activity of PaTPS3 was evaluated as described in the following example.

Example 2

Functional Expression and Characterization of PaTPS3.

The total RNA extracted by Column Plant RNAout kit was first reverse transcribed into cDNA using the SuperScript III First-Strand Synthesis kit (Invitrogen, Shanghai, China). And then the product was used as the template, forward primer (5'-ATGTCTGTCAAAGTTCCTCAATC-3') (SEQ ID NO: 4) and reverse primer (5'-TCACATTGCAATAGGATCGGTG-3') (SEQ ID NO: 5) were used to amplify the gene from the cDNA library of *P. anomala*

The sequences of PaTPS3 was optimized by following the genetic codon frequency of *E. coli* and synthesized. The restriction site of NdeI was added to the 5' end of PaTPS3 while KpnI was added to the 3' end. PaTPS3 was subcloned into the pJ401 (DNA 2.0) plasmid for subsequent expression in *E. coli*.

KRX *E. coli* cells (Promega) were co-transformed with the plasmid pACYC/ScMVA, containing the genes encoding for a heterologous mevalonate pathway, and the plasmid pJ401-PaTPS3. To construct the pACYC/ScMVA plasmid, we divided the eight biosynthetic genes into 2 synthetic operons referred as the 'upper' and 'lower' mevalonate (MVA) pathway. As an upper MVA pathway, we created a synthetic operon consisting of an acetoacetyl-CoA thiolase from *E. coli* encoded by atoB, a HMG-CoA synthase and a truncated version of HMG-CoA reductase from *Saccharomyces cerevisiae* encoded by ERG13 and ERG19, respectively. This operon transforms the primary metabolite Acetyl-CoA into (R)-mevalonate. As a 'lower' mevalonate pathway, we created a second synthetic operon encoding a mevalonate kinase (ERG12, *S. cerevisiae*), a phosphomevalonate kinase (ERGS, *S. cerevisiae*), a phosphomevalonate decarboxylase (MVD1, *S. cerevisiae*), an isopentenyl diphosphate isomerase (idi, *E. coli*) and a farnesyl pyrophosphate (FPP) synthase (IspA, *E. coli*). Finally, a second FPP synthase from *S. cerevisiae* (ERG20) was introduced into the upper pathway operon to improve the conversion of the isoprenoid C5 units (IPP and DMAPP) into farnesyl pyrophosphate (FPP). Each operon was subcloned into one of the multiple-cloning sites of a low-copy expression plasmid under the control of a bacteriophage T7 promoter (pACYCDuet-1, Invitrogen).

Figure 6:
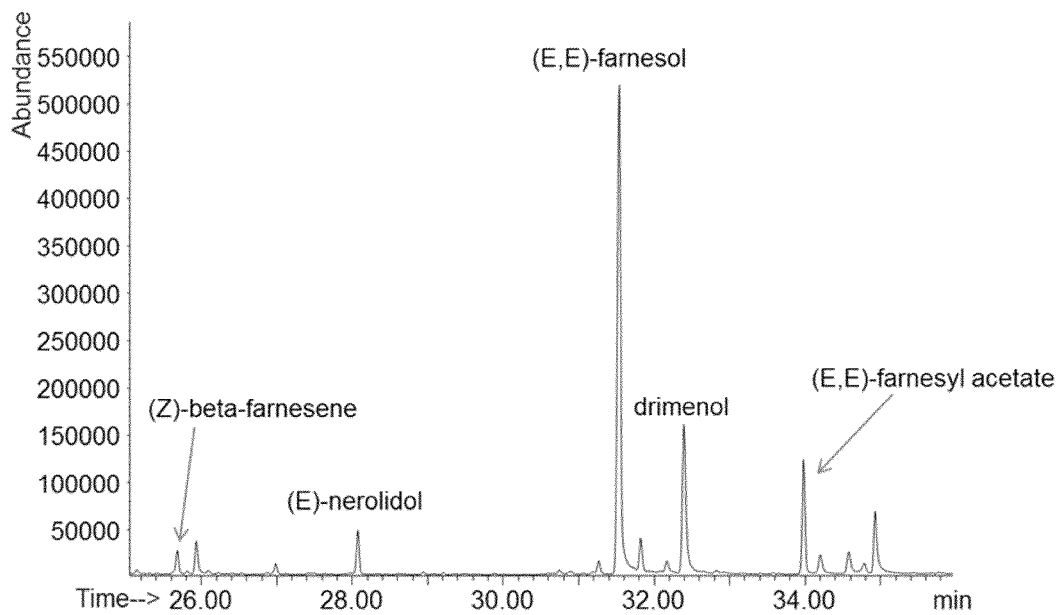
FIG. 6. Shows GC/MS chromatogram of the *E. coli* expression experiment of PaTPS3 (only the zone for sesquiterpene is displayed).
Figure 7:
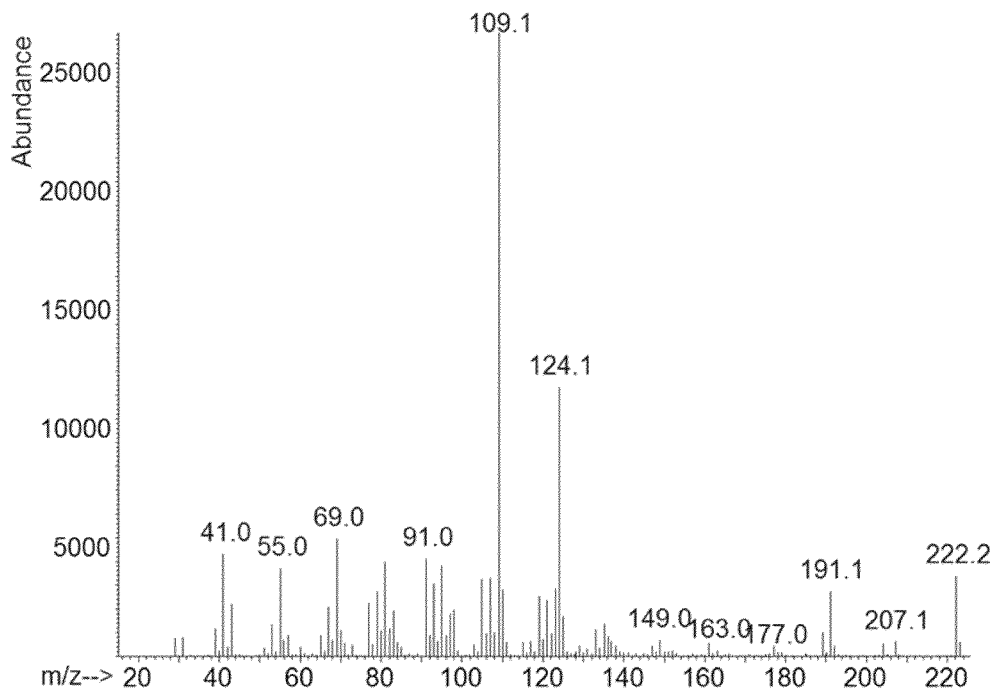
FIG. 7. Shows mass spectrum of the peak of drimenol in FIG. 6.

The co-transformed cells were selected on LB-agar plates containing kanamycin (50 µg/mL final) and chloramphenicol (34 µg/mL final). Single colonies were used to inoculate 5 mL liquid LB medium containing kanamycin (25 µg/mL final) and chloramphenicol (34 µg/mL final). Cultures were incubated overnight at 37° C. and 200 rpm shaking. The next day 6 mL of TB medium supplemented with the same antibiotics and glycerol (3% w/v final) were inoculated with 0.6 mL of the overnight cultures. After 4 hours of incubation at 37° C. and shaking at 200 rpm, the cultures were cooled down to 25° C. for an hour. The volume of the cultures was adjusted to 2 mL for each tube and IPTG (0.1 mM final) was added, overlaid with 200 µL of dodecane. The cultures were incubated for another 48 hours at 25° C. and 200 rpm shaking. The cultures were then extracted with 1 mL ethyl acetate, and 50 µL of isolongifolene (internal standard) at 2 mg/mL was added as internal standard before analysing the samples by GC/MS. GC/MS analysis used the same method as described in Example 1. The carrier gas was helium at a constant flow of 0.7 mL/min. Injection was in split (1:5) mode with the injector temperature set at 250° C. The oven temperature was programmed from 50° C. (5 mM hold) to 300° C. at 5° C./min, then to 340° C. at 50° C./min and held for 3 mM. Identification of products was based on mass spectra and retention indices. GC/MS analysis revealed that PaTPS3 produced drimenol as the main product with a selectivity of 73% (not including farnesol and farnesyl acetate) and a titer of 18.4 mg/L (FIGS. 6 and 7).

Figure 8:
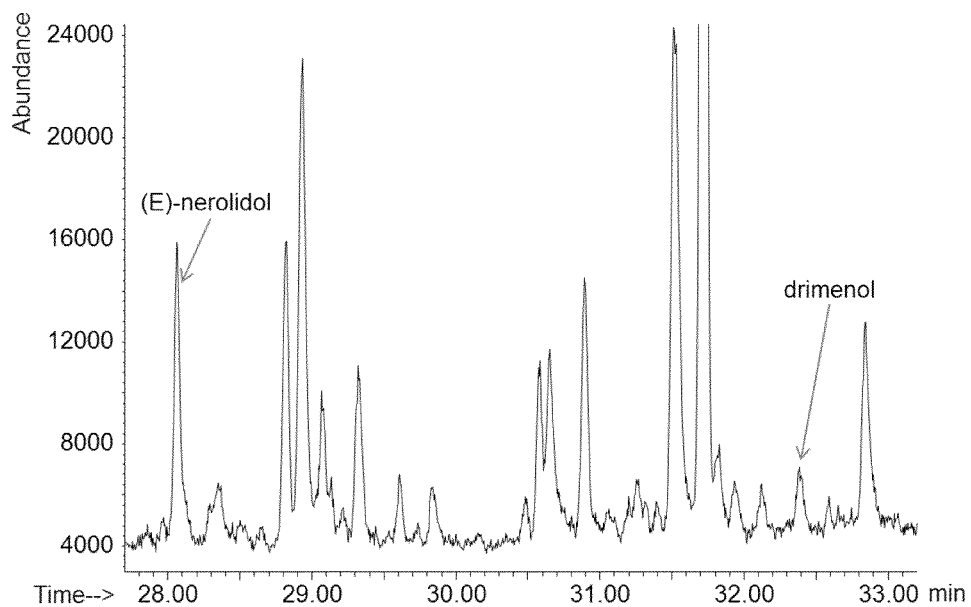
FIG. 8. Shows GC/MS chromatogram of the in vitro assay of PaTPS3 (only the zone for sesquiterpene is displayed).
Figure 9:
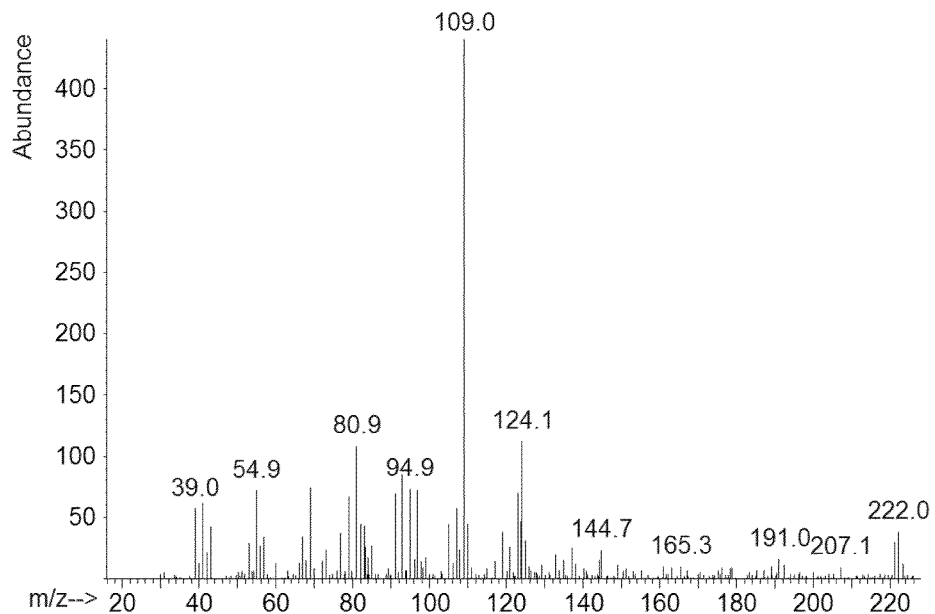
FIG. 9. Shows mass spectrum of the peak of drimenol in FIG. 8.

An in vitro assay was performed to confirm the above in vivo characterization of PaTPS3. BL21 (DE3) *E. coli* cells were transformed with the plasmid pJ401-PaTPS3. The transformed cells were selected on LB-agar plates containing kanamycin (50 µg/mL final). Single colonies were used to inoculate 25 mL liquid LB medium supplemented with the same antibiotic. Cultures were incubated at 37° C. and 200 rpm shaking until turbid (OD around 0.5). After 5 hours of incubation, the cultures were cooled down to 20° C. for 30 min and IPTG (0.1 mM final) was added. The cultures were incubated at 20° C. and 200 rpm overnight, and then centrifuged and re-suspended in 5 mL of 50 mM MOPSO buffer (containing 10% glycerol w/v, and 5 mM DTT, pH 7). The re-suspended cells were broken by sonication on ice for 10 sec for 3 times and centrifuged at 4° C., 12000 rpm for 30 min, the supernatant (containing the crude protein) was used in in vitro assay. A total of 2 mL 50 mM MOPSO reaction buffer (containing 10% glycerol w/v, 15 mM $MgCl_2$, 0.1 mM $MnCl_2$, 1 mM DTT, 6 mM $Na_3VO_4$, pH 7), 10 µL of the 145 µM FPP solution and 1 mL crude protein were mixed and overlaid by 1 mL of heptane, then incubated for 16 hours for in vitro reaction. The reaction was then extracted with 1 mL ethyl acetate, and 50 µL of isolongifolene (internal standard) at 2 mg/mL was added as internal standard before analysing the samples by GC/MS. GC/MS analysis used the same method as described in Example 1. The carrier gas was helium at a constant flow of 0.7 mL/min. Injection was in split (1:5) mode with the injector temperature set at 250° C. The oven temperature was programmed from 50° C. (5 min hold) to 300° C. at 5° C./min, then to 340° C. at 50° C./min and held for 3 min. Identification of products was based on mass spectra and retention indices. GC/MS analysis revealed that PaTPS3 produced drimenol with a selectivity of 21% along with 79% (E)-nerolidol (FIGS. 8 and 9).

```
                    Sequence Listings

SEQ ID NO: 1
cDNA sequence of PaTPS3:
ATGTCTGTCAAAGTTCCTCAATCTCAGAATGCTCCTACAGAGGTTGGACG
TCGGTCCGTAAATTTTCATCCTACTGTTTGGGGAGATCGGTTTATCACAT
ACAATAACCAGTCAGTTGATGATGATGTGGAAAAGAGATTAACAAAAGAA
CTAAAATCCCAAGTGAGGAGAAAGTTGGTGGATGCTGCTGAAAATACATG
TCAGAAGCTTAACACAATCGATGCAATCGAGAGATTAGGCTTGGCTTATC
ATTTCGAAACAGAGATTGAAGAAGCACTGCAAAATATTTATAATTCCTCT
CAGGTTGTTGGAAATAATGTGGAAGAAGATGACCTCTACTCTGTTGCCTT
ACGCTTTAGGCTTCTCAGACAACAGGGCTACAATATTTCATCTGATGTGT
TTAACAAATTCAAAGATGATAAAGATAACTTCAAGGTATCTTTAATTGGT
```

Sequence Listings

```
GATGCATCAAGCTTGCTAAGCCTATATGAAGCTGCACACCTTCGAGTACA
CGGAGAACACATACTGGATGAAGCTCTAACTTTCTCAGTTAATAATCTGG
AATCAATGGCAACCCAATTAAGTCCACCCTTGCAACACATGTAACCCAT
GCACTAAACAGACCACTTCGAAAGGGCATTCCAAGGCTAGAAGCAAGGCA
CTACATTTCTGTCTACGAACAAGATCCTTTACACGATGAAGATCTATTGA
AGCTCGCAAAGTTAGATTTCAACCAATTACAGAAAATTCACCAGAAGGAG
CTAAGCGAGATCTCAAAGTGGTGGAAAGATATAAACTTTGTATCAAAGCT
ACCTTTTGCAAGGGACAGAGTGGTGGAGTGCTACTTTTGGATAATGTCAG
TGCATAGCGAGCCCGAGAACTGGCTTGCACGAAGGACAGCTGCAAAAATA
GCTGCGGTAACCTCCATTATAGATGATATCTATGATGTGCATGGTACAAT
TGACGAACTGACGCTATTTACAGAAGCCGTCAACAGGTGGGATATAAACA
ACATTGATCAACTCCCGGAGTACATGAAAATATGTTATAAGGCGCTCTTG
GGCGTTTTTAGTGAATTAGGGGAAGAGTTGGAAAAACAAGGAAGATCTTA
CCGCCTCGATCATACAATTGAACTTATGAAAGATCTAGTTGGGAACTATT
TTACTGAATCGAAATGGTTAAGCGAAAAATATGTGCCCACAATAGAGGAG
TATATCGTGCTGCAGAAGTCACCATAGGTTACAACAATGCTATAACTGC
ATCTTTTGCCACAGCCAAAGCCGGAGATATTGCAACCAAGGAGACCTTTG
AATGGGTGTTGAGTGAACCTAAAATTGTTAAGGCTTCCTCAGTAATTTGC
AGGTTGATGGATGACTTATCATCCCACAAGTTTGAGCAAAAGAGAGGACA
TGTTGCATCTGCTATTGAATGCTACATGAAGCAACATGATGCTACAGAGG
AAAAGGTGCGTGCGGAGTTTAATAAACAAGTCACCGACGCCTGGAAGGTG
ATAAATCAAGAATGTCTCCACCCAACAGCCATTCCAATGCCTCTTCTTAC
ATGTGTTCTCAACTATGCACGTGTGGCTGATGTCATGTACAAGGATGGAG
ATGCTTATACATTTGCCCAGATCTTACTGAAAGATCATTTATCGGCATTG
TTCACCGATCCTATTGCAATGTGA

SEQ ID NO: 2
Amino acid sequence of PaTPS3:
MSVKVPQSQNAPTEVGRRSVNFHPTVWGDRFITYNNQSVDDDVEKRLTKE
LKSQVRRKLVDAAENTCQKLNTIDAIERLGLAYHFETEIEEALQNIYNSS
QVVGNNVEEDDLYSVALRPRLLRQQGYNISSDVFNKFKDDKDNFKVSLIG
DASSLLSLYEAAHLRVHGEHILDEALTFSVNNLESMATQLSPPLATHVTH
ALNRPLRKGIPRLEARHYISVYEQDPLHDEDLLKLAKLDFNQLQKIHQKE
LSEISKWWKDINFVSKLPFARDRVVECYFWIMSVHSEPENWLARRTAAKI
AAVTSIIDDIYDVHGTIDELTLFTEAVNRWDINNIDQLPEYMKICYKALL
GVFSELGEELEKQGRSYRLDHTIELMKDLVGNYFTESKWLSEKYVPTIEE
YMRAAEVTIGYNNAITASFATAKAGDIATKETFEWVLSEPKIVKASSVIC
RLMDDLSSHKFLQKRGHVASAIECYMKQHDATEEKVRAEFNKQVTDAWKV
INQECLHPTAIPMPLLTCVLNYARVADVMYKDGDAYTFAQILLKDHLSAL
FTDPIAM SEQ ID NO: 3
codon optimized cDNA sequence of PaTPS3 for
expression in E. coli:

ATGTCCGTTAAAGTTCCGCAAAGCCAAAATGCCCCTACCGAAGTTGGCCG
TCGTTCCGTCAACTTCCACCCGACGGTCTGGGGTGATCGTTTCATTACCT
ACAATAACCAGAGCGTTGACGACGATGTGGAAAAGCGTTTGACCAAAGAA
TTGAAGTCCCAGGTCCGTCGTAAACTGGTTGACGCTGCAGAGAACACTTG
CCAGAAACTGAACACCATCGACGCGATCGAGCGCCTGGGTCTGGCTTACC
ATTTCGAGACTGAGATTGAAGAGGCACTGCAGAACATCTACAATTCCAGC
CAAGTCGTGGGCAATAATGTAGAGGAAGATGATTTATATAGCGTGGCGCT
GCGTTTTCGTCTGCTGCGTCAACAGGGTTATAACATCAGCTCCGATGTCT
TTAACAAGTTCAAAGATGATAAAGACAATTTCAAGGTTAGCCTGATCGGT
GACGCAAGCTCTTTGTTATCTCTGTATGAAGCCGCGCATCTGCGCGTGCA
TGGCGAGCATATCTTGGATGAAGCGCTGACCTTTAGCGTTAATAATCTGG
AATCGATGGCAACCCAGCTGAGCCCGCCGCTGGCAACGCACGTTACGCAC
GCGTTGAACCGCCGCTGCGCAAGGGTATCCCGCGTCTGGAAGCGCGTCA
TTACATTTCTGTGTACGAACAAGATCCACTGCACGACGAAGATTTGCTTA
AACTGGCGAAACTGGATTTTAATCAACTGCAAAAGATTCACCAGAAAGAA
CTGAGCGAGATTAGCAAATGGTGGAAAGACATTAATTTCGTCAGCAAGCT
GCCGTTCGCCCGCGACCGTGTTGTGGAGTGCTATTTCTGGATTATGAGCG
TTCACAGCGAGCCTGAGAACTGGCTGGCGCGCCGCACCGCGGCTAAGATT
GCGGCAGTCACGTCGATTATCGACGATATCTATGACGTTCCACGGCACCAT
CGATGACTGACGCTGTTCACCGAAGCCGTTAACCGCTGGGACATCAACA
ACATTGATCAGCTGCCGGAATACATGAAGATCTGCTACAAAGCGCTGCTG
GGCGTGTTCAGCGAGCTGGGTGAAGAACTGGAGAAACAGGGTCGTAGCTA
TCGCTTGGATCATACCATTGAGCTGATGAAAGATCTGGTCGGTAATTACT
TCACCGAGTCCAAGTGGCTGAGCGAGAAATACGTTCCGACGATCGAAGAG
TACATGCGTGCTGCCGAAGTGACCATCGGTTACAACAATGCCATTACGGC
ATCTTTTGCCACGGCAAAGGCCGGTGATATCGCTACCAAAGAAACCTTTG
AATGGGTGCTGAGCGAACCGAAGATTGTCAAAGCCTCCAGCGTTATTTGT
CGTCTGATGGACGATTTGAGCAGCCATAAGTTTCTGCAGAAAAGCGTGGCA
CGTCGCGAGCGCGATCGAGTGCTATATGAAACAGCACGACGCGACCGAGG
AAAAAGTTCGTGCAGAGTTCAATAAACAAGTCACCGATGCGTGGAAAGTC
ATTAACCAAGAGTGCTTGCACCCGACGGCGATCCCGATGCCACTGCTGAC
CTGTGTGCTCAATTATGCACGTGTTGCGGACGTTATGTATAAGGATGGTG
ACGCGTATACCTTTGCGCAAATTCTGCTGAAAGACCACCTGAGCGCACTG
TTCACGGACCCGATCGCGATGTAA

SEQ ID NO: 4
forward primer
ATGTCTGTCAAAGTTCCTCAATC

SEQ ID NO: 5
reverse primer
TCACATTGCAATAGGATCGGTG
```

The invention claimed is:

1. A method for producing drimenol or a mixture comprising drimenol comprising:
   a. transforming a host cell or non-human host organism with a nucleic acid encoding a polypeptide having drimenol synthase activity, wherein the polypeptide comprises an amino acid sequence having at least 95% sequence identity to the amino acid sequence of SEQ ID NO: 2 or comprises the amino acid sequence of SEQ ID NO: 2;
   b. contacting an acyclic farnesyl diphosphate (FPP) precursor with the polypeptide to produce drimenol or a mixture comprising drimenol and one or more terpenes; and
   c. optionally isolating the drimenol; wherein
   the host cell or non-human host organism is a plant, a prokaryote, a fungus, or a microorganism.

2. The method of claim 1, wherein the non-human host organism or the host cell is capable of producing FPP and the non-human host-organism or the host cell is cultured under conditions that allow for the production of the polypeptide.

3. The method of claim 1, further comprising converting the drimenol to a drimenol derivative using chemical synthesis or biochemical synthesis.

4. The method of claim 1, wherein the microorganism is a bacterium or yeast.

5. The method of claim 4, wherein the bacterium is *E. coli* and the yeast is *Saccharomyces cerevisiae*.

6. A method of using a vector comprising an isolated nucleic acid molecule comprising a nucleotide sequence selected from the group consisting of:
   a. a nucleotide sequence encoding an isolated polypeptide having drimenol synthase activity comprising an amino acid sequence having at least 95% sequence identity to the amino acid sequence of SEQ ID NO: 2 or comprising the amino acid sequence of SEQ ID NO: 2;
   b. a nucleotide sequence having at least 95% sequence identity to the nucleotide sequence of SEQ ID NO: 1 or SEQ ID NO: 3 and encoding an isolated polypeptide having drimenol synthase activity; and
   c. the nucleotide sequence of SEQ ID NO: 1 or SEQ ID NO: 3,
   the method comprising transforming a host cell or a non-human organism with the vector and producing drimenol or a mixture comprising drimenol and one or more terpenes; wherein the host cell or the non-human organism is a plant, a prokaryote, a fungus, or a microorganism.

7. The method of claim 6, wherein the mixture comprises drimenol and nerolidol.

8. The method of claim 1, wherein the mixture comprises drimenol and nerolidol.

9. A method of using a vector comprising a nucleic acid encoding a polypeptide having drimenol synthase activity comprising an amino acid sequence having at least 95% sequence identity to the amino acid sequence of SEQ ID NO: 2 or comprising the amino acid sequence of SEQ ID NO: 2, the method comprising transforming a host cell or a non-human organism with the vector and producing drimenol or a mixture comprising drimenol and one or more terpenes; wherein
   the host cell or the non-human organism is a plant, a prokaryote, a fungus, or a microorganism.

10. The method of claim 9, wherein the mixture comprises drimenol and nerolidol.

\* \* \* \* \*